United States Patent [19]

Nakagawa

[11] Patent Number: 4,529,599
[45] Date of Patent: Jul. 16, 1985

[54] TRICYCLIC CARBOXYLATE ESTER AND INSECTICIDE CONTAINING THE SAME

[75] Inventor: Shoji Nakagawa, Tochigi, Japan

[73] Assignee: Kao Corporation, Tokyo, Japan

[21] Appl. No.: 559,700

[22] Filed: Dec. 9, 1983

[30] Foreign Application Priority Data

Dec. 16, 1982 [JP] Japan .............................. 57-220887
Dec. 16, 1982 [JP] Japan .............................. 57-220888

[51] Int. Cl.³ .................. A01N 37/34; C07C 69/753; C07C 121/75
[52] U.S. Cl. .................. 514/511; 260/465 D; 514/421; 514/461; 548/513; 549/499; 560/117
[58] Field of Search .................. 260/465 D; 560/117; 548/513; 549/499; 424/274, 285, 304, 305

[56] References Cited

U.S. PATENT DOCUMENTS 4,169,953 10/1979 Aigami et al. .................. 560/117
4,289,660 9/1981 Schaper et al. .................. 560/117 X

*Primary Examiner*—Dolph H. Torrence
*Attorney, Agent, or Firm*—Birch, Stewart, Kolasch & Birch

[57] ABSTRACT

Carboxylate esters of the formula (I):

$$R_1—COOR_2$$

wherein $R_1$ is a tricyclodecyl or tricycloundecyl group, and $R_2$ is a group of the formula

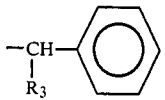

wherein $R_3$ is hydrogen or a cyano group;

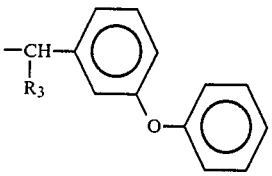

wherein $R_3$ is a hydrogen or a cyano group;

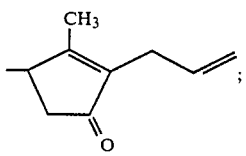

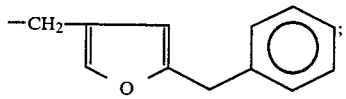

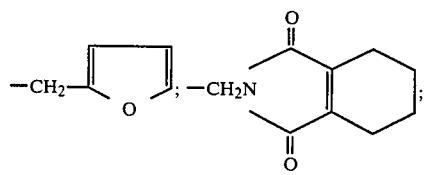

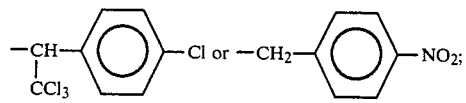

which are useful as insecticides.

20 Claims, No Drawings

TRICYCLIC CARBOXYLATE ESTER AND INSECTICIDE CONTAINING THE SAME

TECHNICAL FIELD

The present invention relates to insecticides, insecticidal compositions, and methods for killing insects.

BACKGROUND ART

Heretofore, many compounds having a tricyclodecane or tricycloundecane skeleton have been synthesized and are drawing attention in the fields of perfumes, insecticides and germicides.

Examples of typical insecticides which have been known for a long time are organic phosphorus insecticides, organic chlorine insecticides and carbamate insecticides.

Among these, the use of some of highly toxic organic phosphorus insecticides and organic chlorine insecticides which are likely to accumulate in the environment, is presently prohibited. Pyrethroid compounds having high safety are used in place of some of these prohibited insecticides together with lowly toxic organic phosphorus insecticides and carbamate insecticides.

Pyrethroid insecticides have advantages in that they have a wide insecticidal spectra, high insecticidal activity and rapid effectiveness, do not allow insects to exhibit resistance and are substantially not harmful to warm-blooded animals. They have, however, disadvantages in that they are unstable and have a tendency to polymerize or to be decomposed or oxidized by high temperature, moisture or light, so that they are lacking in persistence and after-effectiveness. Furthermore, they are highly poisonous to fish and expensive.

Pyrethroid compounds have been used as domestic insecticides, mainly employed indoors, for a long time because of their high safety. For example, a pyrethroid compound having relatively high volatility is used by itself in a mosquito-repellent incense or a mosquito-repellent mat. Furthermore, a pyrethroid compound exhibiting highly rapid effectiveness and one exhibiting high lethality are combined and a synergist is added thereto to prepare an aerosol. Recently, a pyrethroid compound exhibiting both high after-effectiveness and lethality and one exhibiting highly rapid effectiveness are used in combination to prepare a coating aerosol. The pyrethroid insecticides have advantages in that they have a wide insecticidal spectrum, a high insecticidal activity and rapid effectiveness, are almost harmless to warm-blooded animals, and cause insects to exhibit no resistance. They have, however, disadvantages in that they are unstable against heat, light, oxidation and moisture, generally lacking in persistence and after-effectiveness, expensive and highly poisonous to fish. Further, they have the following disadvantages in their applications. Namely, (1) an aerosol comprising a combination of a pyrethroid compound exhibiting rapid effectiveness and one exhibiting high lethality is expensive; (2) though water-based insecticides are recently drawing attention on the basis of a growing recognition that the use of oil-based aerosol insecticides are dangerous, most of the pyrethroid compounds which have been used heretofore are liable to undergo hydrolysis during storage as water-based insecticides, because they are esters of primary alcohols; and (3) when they are used outdoors for gardening, etc., satisfactory effects cannot be obtained with respect to persistence and after-effectiveness by the use of the conventional pyrethroid compounds alone.

DISCLOSURE OF THE INVENTION

The present invention relates to a novel carboxylate ester, and more particularly to a tricyclic carboxylate ester of the formula (I):

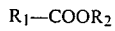

wherein $R_1$ is a tricyclodecyl or tricycloundecyl group, and $R_2$ is a group of the formula

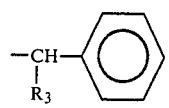

wherein $R_3$ is hydrogen or a cyano group;

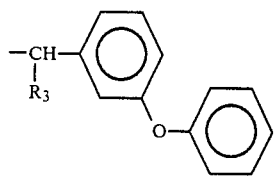

wherein $R_3$ is a hydrogen or a cyano group;

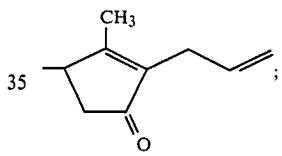

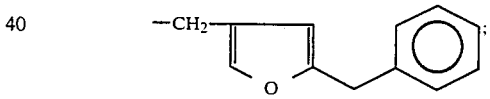

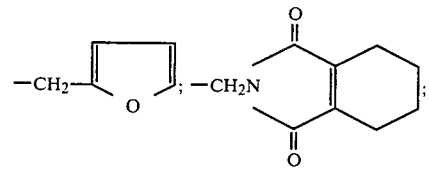

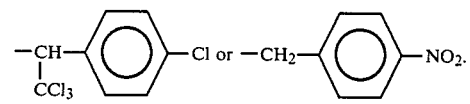

A number of tricyclic carboxylic acids have been synthesized and studied for their activities. It has been discovered, that the compounds of the formula (I) have excellent insecticidal activity, particularly delayed action insecticidal activity. Thus, the delayed activity compounds of the formula (I) are particularly useful in combination with fast acting insecticides such as pyrethroid insecticides.

Among the compounds of the formula (I) α-cyano-3-phenoxybenzyl tricyclo[5.2.1.0$^{2,6}$]decane-2-carboxylate of the formula (8) is especially useful in promoting the insecticidal effect of pyrethroid insecticides.

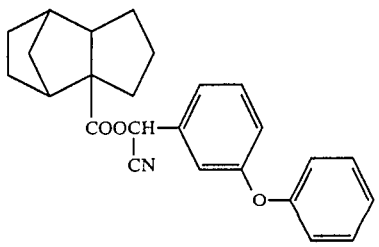

(8)

It has been discovered that the toxicity of the compounds (I) of the present invention against men and animals is low. They have an excellent insecticidal effect on insects such as flies, mosquitos and cockroaches. They are very stable against high temperature, light, moisture and air, and can be used outdoors, whereas the use of the conventional pyrethroid insecticides is primarily limited to indoor use. This stability is evidenced by the fact that the compounds (I) do not undergo hydrolysis, particularly in acidic or alkaline solutions. Furthermore, the compounds of the present invention exhibit proper after-effectiveness and have an insecticidal effect including both delayed action and persistence whereas the conventional pyrethroid insecticides are lacking in these effects. Accordingly, the present invention provides in a first aspect novel tricyclic carboxylate esters of the formula (I) which are useful as insecticides.

In a second aspect, the present invention is directed to insecticidal compositions containing an effective insecticidal amount of at least one of said tricyclic carboxylate esters of the formula (I) and an acceptable carrier therefor. Various insecticide compositions containing the compound of the present invention as an active ingredient (hereinafter referred to as insecticide of the present invention) can be produced by utilizing the above-mentioned characteristics of the compound of the present invention. For example, they can be formulated into insecticides for gardening and discomfort insects as well as those for use under severe conditions, for example, in soil and systemic insecticides to be used for plants rich in water, because of their stability against hydrolysis.

The insecticide of the present invention contains the compound of the present invention at a concentration of 0.01 to 10 weight %, preferably 0.1 to 2 weight %.

The insecticide of the present invention can be used in the form of aerosol or powder spray, and may be in any form of an oil-based and water-based insecticides.

The insecticide of the present invention may contain various chemicals, which are ordinarily used for insecticides, such as known insecticides other than that of the present invention, synergists, or surfactants. For example, although the insecticide of the present invention comprising only the compound of the present invention has an insecticidal effect, this effect can be increased when a synergist such as piperonyl butoxide or cinepyrine 222 for the pyrethroid insecticide is added.

The following unique insecticidal effect can be expected from the insecticide of the present invention because of its delayed action. Namely, even when insects are contacted with the insecticide of the present invention, the insecticidal effect is not immediately exhibited. However, after the insects bring the insecticide back to their nests passively or actively, its effect is slowly exhibited to exterminate gregarious insects such as ants, cockroaches or termites as a whole.

Examples of said pyrethroid insecticides used in the present invention are tetramethrin, kadethrin, permethrin, allethrin, resmethrin, phenothrin, and terarethrin.

The compound of formula (8) exists in the form of endo-trimethylene (6) and exo-trimethylene (7) isomers, thereof. The compound of formula (8) promotes the insecticidal effect of pyrethroid insecticides.

The preferred ratio of a pyrethroid insecticide to the compound of formula (8) in the insecticide composition of the present invention is from 1:1 to 1:100 by weight. The preferred ratio of the pyrethroid insecticide to the compound of formula (8) to piperonyl butoxide is from 1:1:10 to 1:5:50 by weight. The insecticide composition of the present invention can be used in the form of oil-based aerosol, water-based aerosol, powder spray, emulsion, and the like.

When the composition of the present invention is in the form of an oil-based aerosol, the composition contains an effective amount of the compound of the formula (I) and an oil-based carrier which is stored in a suitable aerosol container together with an aerosol propellant. Any suitable oil-based carrier can be utilized. One example of an oil-based carrier is illuminating kerosene. It will be recognized, however, that other oil-based carriers are suitable. Various aerosol propellants can be utilized in accordance with the present invention. A preferred aerosol propellant is liquefied petroleum gas (1 pg). Other aerosol propellants are compounds which are in a liquid state when stored under pressure at room temperature but which vaporize rapidly when released into the atmosphere at room temperature to form an aerosol. Examples of aerosol forming compounds are fluorinated hydrocarbons, preferably fluorinated hydrocarbons having 1 to 3 carbon atoms, such as tetrafluoromethane, hexafluoroethane, difluorodichloromethane and pentafluorochloroethane.

When the composition of the present invention is in the form of a water-based aerosol, the composition contains an effective amount of the compound of the formula (I) and water to form an aqueous solution, dispersion or emulsion which is stored in a container together with an aerosol propellant. The aqueous composition will usually contain a surfactant, dispersant, or emulsifier to aid in the formation of a composition which can be easily sprayed.

When the composition of the present invention is in the form of an emulsion, it contains a compound of the formula (I), a liquid carrier or solvent and an emulsifying agent. The liquid may include water, an inorganic solvent or an organic solvent either alone or in admixture. Exemplary liquid carriers or solvents include water, oils such as kerosene, inorganic solvents, and organic solvents. Exemplary organic solvents include aromatic solvents such as xylene, alcohols, glycols, ketones and the like.

The composition of the present invention may also be in the form of a powder or any other form which may be suitably applied to insects. The carrier is preferably a non-toxic carrier which can be safely used in the presence of humans, animals and/or plant life.

The compositions of the present invention preferably contain, in addition to the slow-acting compounds of the formula (I), an effective amount of a fast acting insecticide such as a pyrethroid insecticide. The pyrethroid insecticide will be present in an amount sufficient to at least temporarily stun an insect but may be present in an effective insecticidal amount sufficient to kill the insect.

Additionally, the compositions of the present invention may contain a compound of the formula (I), preferably the compound of the formula (8), a pyrethroid insecticide and piperonyl butoxide.

In a further aspect, the present invention is directed to a method for killing insects which comprises applying an effective insecticidal amount of the composition of the present invention to an area where insects are present. The composition is preferably applied directly to the insects either in any growth stage such as the larva or mature stage.

The insecticidal compositions of the present invention have the following advantages:

(1) An insecticidal effect can be obtained even at a low concentration at which no sufficient insecticidal effect can be obtained when a pyrethroid insecticide is used alone. For example, a composition containing tetramethrin exhibiting excellent rapid effectiveness among the pyrethroid compounds, the compound of formula (8) and piperonyl butoxide has a surprisingly high insecticidal effect on house fly (*Musca domestica Linné*) as compared with cases where each compound is used alone.

(2) Since aerosols for gardening or discomfort harmful insects are used outdoors and exposed under outdoor weather conditions, their effectiveness can not persist, if they comprise unstable ingredients. In contrast, since the insecticide composition of the present invention contains such a stable ingredient as the compound of formula (8), the persistance of its effectiveness can be expected.

(3) Even when the insecticide composition is formulated as a water-based aerosol or spray by using the compound of formula (8) stable against hydrolysis, piperonyl butoxide and a pyrethroid insecticide, particularly a pyrethroid insecticide composed of a secondary alcohol, such as allethrin, an insecticidal effect including both excellent rapid effectiveness and persistence can be obtained. Upon application to insects, insects are knocked down by the rapid-effective pyrethroid compound. The effect is caused to persist by piperonyl butoxide, and the compound of formula (8) slowly functions. Thus a potent insecticidal effect can be expected.

(4) Expensive pyrethroid compounds can be saved by using an inexpensive compound of formula (8) and piperonyl butoxide.

(5) When an oil-based aerosol is sprayed on plants, there is a possibility that they will be damaged, for example, by kerosene which is often an ingredient thereof. However, the plants are not damaged by the water-based aqueous compositions of the present invention and are safe.

The tricyclic carboxylate ester of the present invention can be produced, for example, by reacting a tricyclic carboxylic acid (II) or a reactive derivative thereof with an alcohol (III) according to the following reaction:

$$R_1COOH + R_2OH \longrightarrow R_1-COOR_2$$
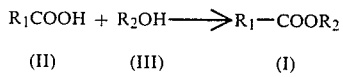

wherein $R_1$ and $R_2$ are as defined above.

This reaction can be conducted by a conventional esterification reaction. Examples of the reactive derivatives of the carboxylic acid (II) include acid halides, acid anhydrides, mixed acid anhydrides and active esters. For example, when an acid halide of the compound (II) is used, the halide is reacted with an alcohol (III) in the presence of an acid acceptor such as pyridine or triethylamine in an anhydrous solvent such as benzene, toluene or ethyl acetate at room temperature to 130° C. for several hours to several days. When the tricyclic carboxylic acid is directly reacted with an alcohol, it is preferred to carry out the reaction in the presence of a condensing agent such as dicyclohexylcarbodiimide (DCC).

Typical compounds (I) of the present invention produced by the above method are as follows.

| Compound No. | Structure | |
|---|---|---|
| (1) | 3-phenoxybenzyl endo-tricyclo[5.2.1.0²,⁶]-decane-2-exo-carboxylate | $n_D^{21}$ 1.5651 |
| (2) | 3-phenoxybenzyl exo-tricyclo[5.2.1.0²,⁶]-decane-2-endo-carboxylate | $n_D^{22}$ 1.5628 |
| (3) | 3-phenoxybenzyl endo-tricyclo[5.2.1.0²,⁶]-decane-8-exo-carboxylate | $n_D^{22}$ 1.5681 |
| (4) | 3-phenoxybenzyl tricylco[3.3.1.1³,⁷]decane-1-carboxylate | $n_D^{21}$ 1.5705 |

| Compound No. | Structure | |
|---|---|---|
| (5) | 3-phenoxybenzyl tricylco[4.3.1.1$^{2,5}$]undecane-1-carboxylate | $n_D^{22}$ 1.5720 |
| (6) | α-cyano-3-phenoxybenzyl endo-tricyclo-[5.2.1.0$^{2,6}$]decane-2-exo-carboxylate | $n_D^{20}$ 1.5654 |
| (7) | α-cyano-3-phenoxybenzyl exo-tricyclo-[5.2.1.0$^{2,6}$]decane-2-endo-carboxylate | $n_D^{22}$ 1.5657 |
| (8) | α-cyano-3-phenoxybenzyl tricyclo[5.2.1.0$^{2,6}$]-decane-2-carboxylate | $n_D^{21}$ 1.5641 |
| (9) | α-cyano-3-phenoxybenzyl endo-tricyclo-[5.2.1.0$^{2,6}$]decane-8-exo-carboxylate | $n_D^{21}$ 1.5653 |
| (10) | α-cyano-3-phenoxybenzyltricyclo[3.2.1.1$^{3,7}$]-decane-1-carboxylate | m.p. 115~121° C. |
| (11) | α-cyano-3-phenoxybenzyl tricyclo[4.3.1.1$^{2,5}$]-undecane-1-carboxylate | $n_D^{21}$ 1.5701 |
| (12) | α-cyano-3-phenoxybenzyl tricyclo[5.3.1.0$^{3,8}$]-undecane-3-carboxylate | $n_D^{22}$ 1.5647 |
| (13) | 5-benzyl-3-furylmethyl-endo-tricyclo-5.2.1.0$^{2,6}$]decane-2-exo-carboxylate | $n_D^{22}$ 1.5463 |
| (14) | 5-benzyl-3-furylmethyl-exo-tricyclo-[5.2.1.0$^{2,6}$]decane-2-endo-carboxylate | $n_D^{22}$ 1.5440 |
| (15) | 2-allyl-4-methyl-2-cyclopenten-1-on-4-yl endo-tricyclo[5.2.1.0$^{2,6}$]decane-2-exo-carboxylate | $n_D^{22}$ 1.5252 |

| Compound No. | Structure | |
|---|---|---|
| (16) | 2-allyl-4-methyl-2-cyclopenten-1-on-4-yl-exo-tricyclo[5.2.1.0²,⁶]decane-endo-carboxylate | $n_D^{22}$ 1.5211 |
| (17) | 3,4,5,6-tetrahydrophthalimidomethyl endo-tricyclo[5.2.1.0²,⁶]decane-2-exo-carboxylate | $n_D^{22}$ 1.5350 |
| (18) | 3,4,5,6-tetrahydrophthalimidomethyl exo-tricyclo[5.2.1.0²,⁶]decane-2-endo-carboxylate | $n_D^{22}$ 1.5299 |
| (19) | benzyl endo-tricyclo[5.2.1.0²,⁶]decane-2-exo-carboxylate | $n_D^{22}$ 1.5381 |
| (20) | α-cyanobenzyl endo-tricyclo[5.2.1.0²,⁶]decane-2-exo-carboxylate | $n_D^{22}$ 1.5371 |
| (21) | α-trichloromethyl-4-chlorobenzyl endo-tricyclo-[5.2.1.0²,⁶]decane-2-exo-carboxylate | m.p. 125–128° C. |
| (22) | 4-nitrobenzyl endo-tricyclo[5.2.1.0²,⁶]decane-2-exo-carboxylate | $n_D^{21}$ 1.5580 |
| (23) | 2-furylmethyl endo-tricyclo[5.2.1.0²,⁶]decane-2-exo-carboxylate | $n_D^{22}$ 1.5166 |

DESCRIPTION OF THE PREFERRED EMBODIMENTS

EXAMPLE 1

Synthesis of α-cyano-3-phenoxybenzyl endo-tricyclo-[5.2.1.0²,⁶]decane-2-exo-carboxylate (compound No. 6)

50 g (0.28 mol) of endo-tricyclo[5.2.1.0²,⁶]decane-2-exo-carboxylic acid was dissolved in 110 ml of anhydrous benzene. 100 g (0.84 mol) of thionyl chloride was added dropwise thereto. The mixture was stirred with heating at 100° C. for 5 hours. Then the solvent was removed under reduced pressure. Vacuum distillation was conducted to give 51.5 g (yield 93.5%) of endo-tricyclo[5.2.1.0²,⁶]decane-2-exo-carbonyl chloride with b.p. of 67° C./0.18 mmHg.

2.54 g (11.3 mmol) of α-cyano-3-phenoxybenzyl alcohol was dissolved in 20 ml of anhydrous benzene and 1.78 g (22.5 mmol) of anhydrous pyridine and 2.24 g (11.3 mmol) of the acid chloride prepared above were added thereto. The mixture was stirred with heating at 100° C. for 46 hours. After the completion of the reaction, precipitated pyridine hydrochloride was removed by filtration and the filtrate was thoroughly washed with 1 N hydrochloric acid, 5% sodium carbonate, and then saturated saline solution, and dried over sodium sulfate. The solvent was removed under reduced pressure to obtain 4.3 g of a viscous oily material. Vacuum distillation was conducted with a Kugel roll to afford 3.0 g (yield 68.5%) of a viscous yellow oily material with b.p. of 227°–230° C./0.07 mmHg.

IR (liquid film): 2950, 2870, 1740, 1580, 1480, 1250 1210, 1150, 1020, 780, 750, 690 cm⁻¹

¹H NMR (solvent: CCl₄, internal reference: TMS, δ ppm)

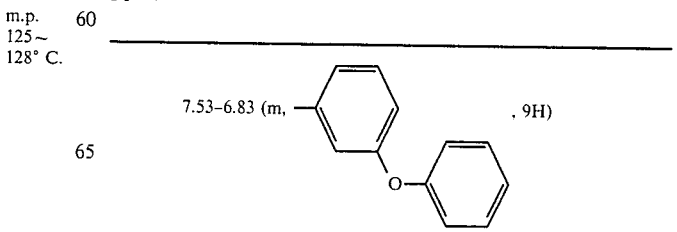

7.53–6.83 (m, —⌬—O—⌬, 9H)

6.30 (s, —COOCH(CN)—, 1H)
2.90–1.00 (m, ring, 15H)

MS (relative intensity) 387($M^{30}$, 6), 181(12), 163(26), 136(11), 135(100), 95(7), 93(10), 91(7), 81(6), 79(9) 77(9), 67(32), 51(5), 41(8)

EXAMPLE 2

Synthesis of 3-phenoxybenzyl exo-tricyclo[5.2.1.0$^{2,6}$]-decane-2-endo-carboxylate (compound No.2)

1 g (5.55 mmol) of exo-tricyclo[5.2.1.0$^{2,6}$]decane-2-endo-carboxylic acid and 3.2 g (26.90 mmol) of thionyl chloride were stirred in 10 ml of anhydrous benzene with heating at 100° C. for 5 hours. Thereof, the mixture was left to stand overnight and the solvent and unreacted thionyl chloride were removed with an aspirator and further a vacuum pump. 10 ml of anhydrous benzene was added to the residue and 1.1 g (5.49 mmol) of 3-phenoxybenzyl alcohol dissolved in 30 ml of anhydrous benzene and 0.87 g (11.00 mmol) of anhydrous pyridine were added thereto. The mixture was stirred with heating at 100° C. for 15 hours and then cooled. The precipitated pyridine hydrochloride was removed by filtration and the filtrate was thoroughly washed with 1N hydrochloric acid, 5% sodium carbonate, and then saturated saline solution, and dried over sodium sulfate. The solvent was removed under reduced pressure to obtain 2 g of an oily material. Purification by column chromatography on silica gel employing a developer consisting of benzene and n-hexane (1:1) gave 1.64 g (yield 81.6%) of a colorless oily material.

IR (liquid film): 3080, 3050, 2960, 2880, 1730, 1580, 1480, 1450, 1260, 1220, 1160, 1020, 770, 750, 680 cm$^{-1}$ $^1$H NMR (solvent: CDCl$_3$, internal reference: TMS, δ ppm)

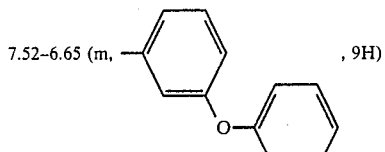

5.06 (s, —COOCH$_2$—, 2H)
2.60–0.60 (m, ring, 15H)

MS (relative intensity) 362($M^{30}$, 22), 184(25), 183(47), 164(7), 163(52), 136(12), 135(100), 113(8), 95(8), 93(12), 91(10), 89(7), 79(11), 77(11), 67(49), 65(7), 41(10)

EXAMPLE 3

Synthesis of 3-phenoxybenzyl endo-tricyclo[5.2.1.0$^{2,6}$]decane-8-exo-carboxylate (compound No. 3)

1 g (5.03 mmol) of endo-tricyclo[5.2.1.0$^{2,6}$]decane-8-exo-carbonyl chloride, 1 g (4.99 mmol) of 3-phenoxybenzyl alcohol and 0.79 g (9.99 mmol) of anhydrous pyridine were stirred in 40 ml of anhydrous benzene at room temperature for 18 hours. Then the reaction was terminated. The precipitated pyridine hydrochloride was removed by filtration and the filtrate was thoroughly washed with 1N hydrochloric acid, saturated aqueous sodium bicarbonate solution, and then saturated saline solution, and dried over sodium sulfate. The solvent was removed to obtain 1.8 g of an oily material. Purification by column chromatography on silica gel employing a developer consisting of benzene and n-hexane (1:1) gave 1.26 g (yield 69.6%) of a colorless oily material.

IR (liquid film): 3070, 3050, 2960, 2880, 1730, 1580, 1480, 1450, 1260, 1210, 1160, 1020, 770, 750, 680 cm$^-$ $^1$H NMR (solvent:CDCl$_3$, internal reference: TMS, δ ppm)

7.52–6.65 (m, —⌬—O—⌬, 9H)

5.02 (s, —COOCH$_2$—, 2H)
2.78–1.05 (m, ring, 15H)

MS (relative intensity) 362($M^+$, 32), 200(54), 198(15), 183(37), 163(20), 136(12), 135(100), 93(14), 79(11), 77(12), 67(56), 41(15)

EXAMPLE 4

Synthesis of 3-phenoxybenzyl tricyclo[3.3.1.1$^{3,7}$]decane-1-carboxylate (compound No. 4)

1 g (5.03 mmol) of tricyclo[3.3.1.1$^{3,7}$]decane-1-carbonyl chloride, 1.01 g (5.04 mmol) of 3-phenoxybenzyl alcohol and 0.08 g (10.07 mmol) of anhydrous pyridine were dissolved in 30 ml of anhydrous benzene. The mixture was stirred at room temperature for 66 hours. Then the reaction was terminated. The resulting pyridine hydrochloride was removed by filtration and the filtrate was thoroughly washed with 1N hydrochloric acid, 5% sodium carbonate and then saturated saline solution, and dried over sodium sulfate. The solvent was removed to obtain 1.8 g of an oily material. Purification by column chromatography on silica gel employing a developer consisting of n-hexane and benzene (1:1) gave 1.69 g (yield 93%) of a colorless oily material.

IR (liquid film): 3070, 3050, 2910, 2850, 1730, 1580, 1480, 1450, 1250, 1220, 1070, 770, 750, 680 cm$^{-1}$ $^1$H NMR (solvent: CCl$_4$, internal reference: TMS, δ ppm)

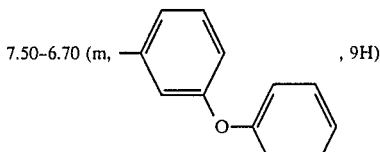

4.97 (s, —COOCH$_2$—, 2H)
2.22–1.52 (m, ring, 15H)

MS (relative intensity) 362($M^{30}$, 19), 198(10), 183(11), 136(12), 135(100), 93(13), 79(14)

EXAMPLE 5

Synthesis of 5-benzyl-3-furylmethyl endo-tricyclo[5.2.1.0²,⁶]decane-2-exo-carboxylate (compound No. 13)

1 g (5.03 mmol) of endo-tricyclo[5.2.1.0²,⁶]decane2-exo-carbonyl chloride, 0.95 g (5.05 mmol) of 5-benzyl3-furylmethyl alcohol and 0.80 g (10.11 mmol) of anhydrous pyridine were dissolved in 30 ml of anhydrous benzene. The mixture was stirred with heating at 100° C. for 28 hours and then filtered. The filtrate was thoroughly washed with 1N hydrochloric acid, 5% sodium carbonate and then saturated saline solution, and dried over sodium sulfate. The solvent was removed to obtain 1.8 g of an oily material. Purification by column chromatography on silica gel employing a developer consisting of n-hexane and benzene (2:1 or 1:1) gave 1.52 g (yield 86.4%) of an oily material.

IR (liquid film): 3070, 3040, 2950, 2880, 1720, 1600, 1550, 1500, 1450, 1220, 1160, 1030, 800, 730, 700 cm⁻¹

¹H NMR (solvent: CDCl₃, internal reference: TMS, δ ppm)

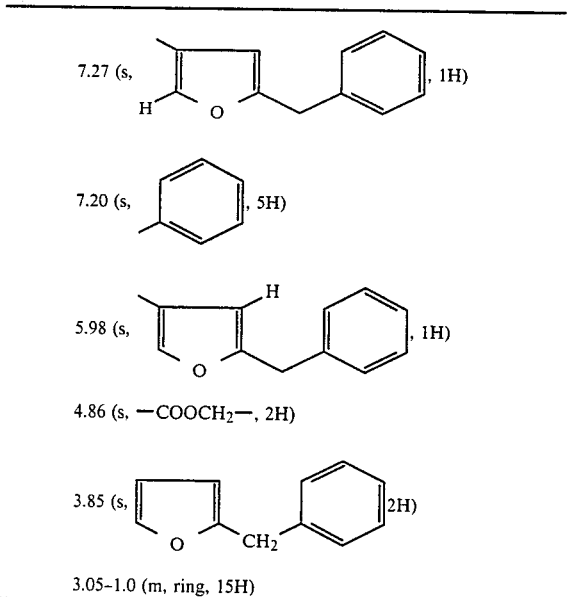

MS (relative intensity) 350(M⁺, 5), 172(5), 171(6), 164(5), 163(33), 143(9), 141(5), 136(11), 135(100), 128(12), 115(5), 95(5), 93(9), 91(12), 81(6), 79(8), 67(28), 65(5), 41(6)

EXAMPLE 6

Synthesis of 2-allyl-4-methyl-2-cyclopenten-1-on-4-yl endo-tricyclo[5.2.1.0²,⁶]decane-2-exo-carboxylate (compound No. 15)

1.31 g (6.54 mmol) of endo-tricyclo[5.2.1.0²,⁶]-decane-2-exo-carbonyl chloride, 1.00 g (6.57 mmol) of allethrolone (2-allyl-4-methyl-2-cyclopenten-1-on-4-ol) and 1.04 g (13.15 mmol) of anhydrous pyridine were dissolved in 30 ml of anhydrous benzene. The mixture was stirred with heating at 100° C. for 23 hours and then filtered. The filtrate was thoroughly washed with 1N hydrochloric acid, 5% sodium carbonate and then saturated saline solution, and dried over sodium sulfate. The solvent was removed to obtain 1.9 g of an oily material. Purification by column chromatography on silica gel employing a developer consisting of n-hexane and benzene (1:1 to 1:4) gave 1.78 g (yield 86.6%) of an oily material.

IR (liquid film): 3090, 2960, 2880, 1730, 1710, 1650, 1400, 1220, 1150, 990, 910 cm⁻¹

¹H NMR (solvent: CDCl₃, internal reference: TMS, δ ppm)

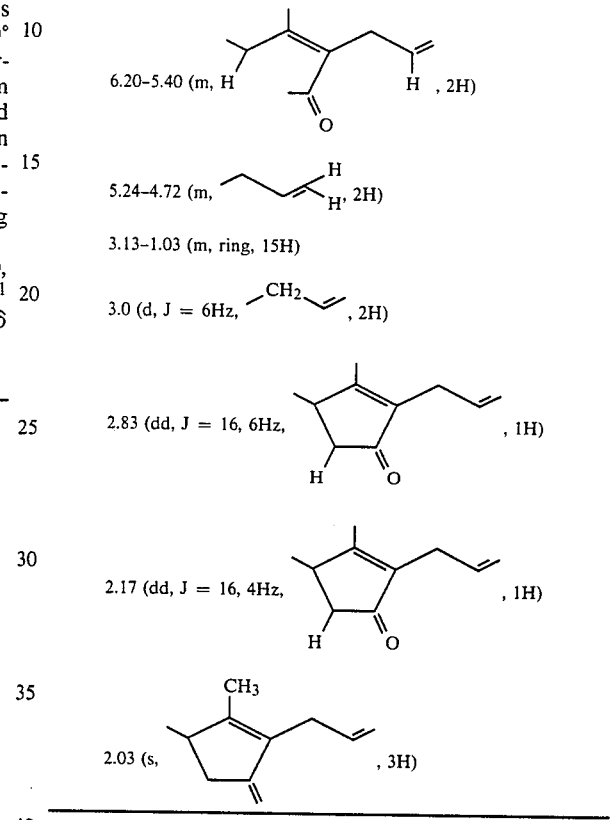

MS (relative intensity) 314(M⁺, 14), 163(8), 136(27), 135(100), 134(49), 107(19), 93(26), 91(25), 81(10), 79(33), 77(12), 67(60), 65(8), 41(18), 39(9)

EXAMPLE 7

Synthesis of α-cyano-3-phenoxybenzyl exo-tricyclo-[5.2.1.0²,⁶]decane-2-endo-carboxylate (compound No. 7)

1 g (5.55 mmol) of exo-tricyclo[5.2.1.0²,⁶]decane-2-endo-carboxylic acid and 3.4 g (28.58 mmol) of thionyl chloride in anhydrous benzene were stirred with heating at 100° C. for 7 hours. Then the solvent and unreacted thionyl chloride were removed. 1.79 g (5.56 mmol) of α-cyano-3-phenoxybenzyl alcohol and 0.88 g (11.13 mmol) of anhydrous pyridine were added to the residue. The mixture was stirred in 30 ml of anhydrous benzene with heating at 100° C. for 15 hours and then filtered. The filtrate was thoroughly washed with 1N hydrochloric acid, 5% sodium carbonate and then saturated saline solution, and dried over sodium sulfate. The solvent was removed to obtain 2.0 g of an oily material. Purification by column chromatography on silica gel employing a developer consisting of benzene and n-hexane gave 1.0 g (yield 46.5%) of an oily material.

IR (liquid film): 2940, 2860, 1730, 1580, 1480, 1440, 1230, 1200, 1140, 1010, 770, 750, 680 cm⁻¹ ¹H NMR (solvent: CCl₄, internal reference: TMS, δ ppm)

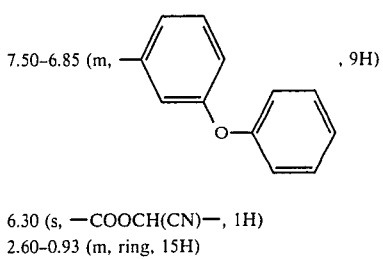

7.50–6.85 (m, —⌬—O—⌬, 9H)

6.30 (s, —COOCH(CN)—, 1H)
2.60–0.93 (m, ring, 15H)

MS (relative intensity) 387(M+, 6), 181(13), 163(43), 136(11), 135(100), 95(7), 93(8), 91(7), 79(9), 77(9), 67(36), 41(8)

EXAMPLE 8

Synthesis of δ-cyano-3-phenoxybenzyl tricyclo-[5.2.1.0²,⁶]decane-2-carboxylate (compound No. 8)

2.08 g (11.54 mmol) of tricyclo[5.2.1.0²,⁶]decane-2-carboxylic acid (a mixture composed of the endo- and the exo-carboxylic acids in a ratio of 31:69) and 5.7 g (47.91 mmol) of thionyl chloride were stirred in 10 ml of anhydrous benzene with heating at 100° C. for 4 hours. Then the solvent and unreacted thionyl chloride were removed. 2.60 g (11.54 mmol) of α-cyano-3-phenoxybenzyl alcohol and 1.83 g (23.14 mmol) of anhydrous pyridine were added to the residue. The mixture was stirred in 30 ml of anhydrous ethyl acetate at room temperature for 4 days, and further at 100° C. for 70 hours. The reaction was terminated when it did no longer proceed. The reaction solution was filtered and the filtrate was thoroughly washed with 1N hydrochloric acid, 5% sodium carbonate and then saturated saline solution, and dried over sodium sulfate. The solvent was removed to obtain 4.11 g of a brownish oily material. Purification by column chromatography on silica gel employing a developer consisting of n-hexane and benzene (2:1) gave 2.3 g (51.4%) of a yellowish oily material. The ratio of the ester originated from the endo-carboxylic acid to that originated from the exo-carboxylic acid was 8.3:91.7.

IR (liquid film): 2960, 2890, 1740, 1580, 1480, 1440, 1240, 1210, 1140, 1020, 780, 750, 680 cm⁻¹

¹H NMR (Solvent: CDCl₃, internal reference: TMS, δ ppm)

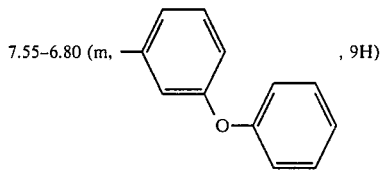

7.55–6.80 (m, —⌬—O—⌬, 9H)

6.34 (s, —COOCH(CN)—, 1H)
2.90–1.00 (m, ring, 15H)
MS (relative intensity)

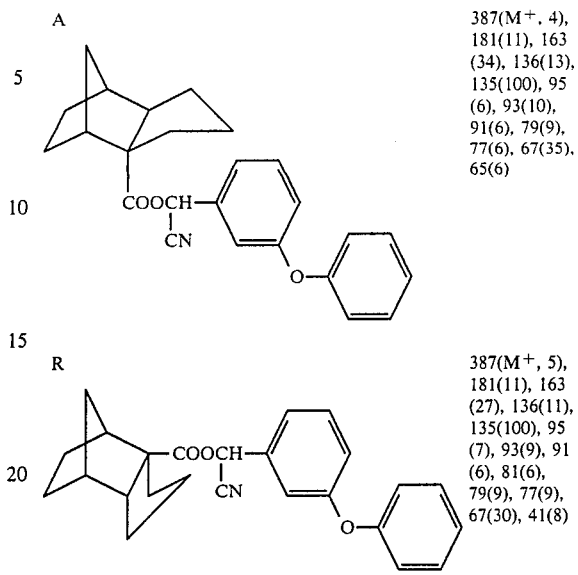

A  387(M+, 4), 181(11), 163 (34), 136(13), 135(100), 95 (6), 93(10), 91(6), 79(9), 77(6), 67(35), 65(6)

R  387(M+, 5), 181(11), 163 (27), 136(11), 135(100), 95 (7), 93(9), 91 (6), 81(6), 79(9), 77(9), 67(30), 41(8)

EXAMPLE 9

Synthesis of α-cyanobenzyl endo-tricyclo[5.2.1.0²,⁶]decane-2-exo-carboxylate (compound No. 20)

1 g (5.03 mmol) of endo-tricyclo[5.2.1.0²,⁶]decane-2-exo-carbonyl chloride, 0.67 g (5.03 mmol) of α-cyanobenzyl alcohol (mandelonitrile) and 0.80 g (10.11 mmol) of anhydrous pyridine were stirred in 20 ml of anhydrous toluene with heating at 130° C. for 9 hours. The mixture was cooled and filtered. The filtrate was thoroughly washed with 1N hydrochloric acid, 5% sodium carbonate and then saturated saline solution, and dried over sodium sulfate. The solvent was removed to obtain 1.4 g of an oily material. The oily material was distilled by means of a Kugel roll to give 0.97 g (yield 65%) of an oily material with b.p. of 150° C./0.5 mmHg.

IR (liquid film): 3080, 3050, 2960, 2890, 1740, 1600, 1590, 1450, 1210, 1150, 750, 690 cm⁻¹

¹H NMR (solvent: CDCl₃, internal reference: TMS, δ ppm)

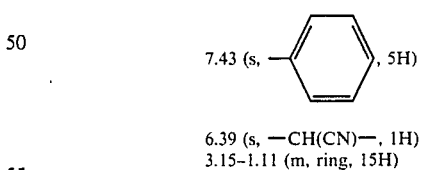

7.43 (s, —⌬, 5H)

6.39 (s, —CH(CN)—, 1H)
3.15–1.11 (m, ring, 15H)

MS (relative intensity) 295(M+, 9), 163(31), 136(12), 135(100), 133(12), 116(35), 93(20), 91(15), 89(10), 81(12), 79(21), 77(11), 67(65), 41(17)

Example 10—House Fly

Insecticidal Test Against House Fly by the Ultralow Volume Dropping Method

An acetone solution containing the compound of the present invention at a concentration given in Table 1 was applied to the backboard of the breast of each female imagines of house fly (*Musca domestica Linné*), three- to five-day-old after emergence, anesthetized with carbon dioxide gas, by means of an Arnolds's manual ultralow volume dropping device. The treated house flies were placed in a deep petri dish of 9 cm in diameter and 6 cm in height, on which bottom a filter paper was laid. Absorbent cotton containing 2% sugared water was placed in a container made of aluminum foil, and given as a feed to the flies. The top of the dish was covered with gauze. 50 house flies (two groups; each composed of 25 flies) were left to stand in a room at about 23° C. After 24 and 48 hours, it was observed whether they were living or dead, to determine the lethality rate. The results are given in Table 1.

TABLE 1

| Compound Tested Compound of present invention | Lethality rate (%) at specified doses after specified hours | | | |
|---|---|---|---|---|
| | 10 μg | | 100 μg | |
| | 24 hr | 48 hr | 24 hr | 48 hr |
| 2 | 6 | 6.1 | 8 | 8.2 |
| 6 | 16 | 16.1 | 86 | 98 |
| 7 | 16 | 12 | 62 | 76 |
| 8 | 12.2 | 18.4 | 98 | 97.9 |
| 13 | — | — | 4 | 10.6 |
| 14 | — | — | 12 | 36.2 |
| 15 | — | — | 68 | 80.9 |
| 23 | — | — | 4 | 14.3 |

Example 11

$LD_{50}$ Values Determined by the Ultralow Volume dropping method

In the same manner as in Example 10, the lethality rates of house flies at specified doses were determined 24 and 96 hours after the application of each of compounds No. 6 and No. 7 of the present invention. $LD_{50}$ values after 24 and 96 hours were determined by a Profit diagrammatic method. The results are given in Table 2.

TABLE 2

| Compound tested | $LD_{50}$ (μg) | |
|---|---|---|
| | 24 hr | 96 hr |
| compound No. 6 of present invention | 35 | 23 |
| compound No. 7 of present invention | 190 | 86 |
| allethrin | 3.2 | 3.2 |

Example 12—House Mosquito

Insecticial Test Against Pale House Mosquito by the Ultralow Volume Dropping Method An acetone solution containing the compound of the present invention at a concentration given in Table 3 was applied to the backboard of the breast of each of female imagines of pale house mosquito (*Culex Pipens Pallens Coquillet*), anesthetized with carbon dioxide gas, by an Arnold's manual ultralow volume dropping device. The treated mosquitos were placed in a deep petri dish of 9 cm in diameter and 6 cm in height, on which bottom a filter paper was laid. Absorbent cotton containing 2% sugared water was placed in a container made of aluminum foil, and given as a feed to them. The top of the dish was covered with gauze. 50 mosquitos (two groups; each composed of 25 mosquitos) were left to stand in a room at about 23° C. After 24 and 48 hours, it was observed whether they were living or dead, to determine the lethality rate. The results are given in Table 3.

TABLE 3

| Compound Tested Compound of present invention | Lethality rate (%) at specified doses after specified hours | | | |
|---|---|---|---|---|
| | 5 μg | | 50 μg | |
| | 24 hr | 48 hr | 24 hr | 48 hr |
| 2 | — | — | 6 | 6 |
| 6 | 15.1 | 12.1 | 44 | 68 |
| 7 | 11.1 | 11.2 | 98 | 98 |
| 8 | 24 | 26 | 54 | 52 |
| 14 | — | — | 14 | 22 |
| 15 | — | — | 98 | 100 |
| 17 | — | — | 50 | 52 |

Example 13—German Cockroach

Insecticidal Test Against German Cockroach by the Ultralow Dropping Method

An acetone solution containing each of 10% and 1% of compound No. 8 of the present invention was applied around the midlegs of the breast on the abdominal side of each of male imagines of German cockroach (*Blattella germanica Linné*) anesthetized with carbon dioxide gas, by an Arnold's manual ultralow volume dropping device. The treated cockroaches were placed in an ice cream cup having a 200-ml volume. Absorbent cotton containing 2% sugared water was given as a feed to them. The cup was covered with a lid through which fresh air could be freely passed. 45 cockroaches (three groups; each composed of 15 cockroaches) were left to stand in a room at about 23° C. After 7 days, it was observed whether they were living or dead. The lethality rates of 97.7% at a dose of 200 μg and 7.9% at a dose of 20 μg were obtained.

Example 14

Increase in an Insecticidal Effect on Female Imagines of House Fly by the Addition of Piperonyl Butoxide to Compound No. 8 of the Present Invention In a similar manner to that described in Example 10, the insecticidal rate of female imagines of house flies after 24 hours was determined by adding piperonyl butoxide (PB) (a synergist of the pyrethroid) to compound No. 8 of the present invention. The insects tested were 50 flies (two groups; each composed of 25 flies). The results are given in Table 4.

TABLE 4

| Compound tested | Insecticidal rate (%) | | | |
|---|---|---|---|---|
| | PB (0 μg) | PB (2 μg) | PB (5 μg) | PB (10 μg) |
| — | | 0 | 0 | 0 |
| compound No. 8 of present invention | | | | |
| (0.5 μg) | | | 64 | |
| (1 μg) | 0 | 63.3 | 95.9 | 100 |
| (10 μg) | 12.2 | | | |
| allethrin | | | | |
| (0.5 μg) | 0 | | | |
| (1 μg) | 18.4 | | | |

It is apparent from the table that the insecticidal effect obtained by the synergistic action of compound No. 8 and piperonyl butoxide is superior to that of allethrin. Therefore, it is clear that the use of the compound of the present invention in combination with the synergist is very effective.

Example 15—German Cockroach

Increase in an Insecticidal Effect on Male Imagines of German Cockroach by the Addition of Piperonyl Butoxide to Compound 8 of the Present Invention In a similar manner to be described in Example 13, the insecticidal rates of male imagines of the cockroaches after 7 days were determined by using compound No. 8 and piperonyl butoxide (PB) (a synergist of the pyrethroid) in combination. The insects tested were 45 cockroaches (three groups; each composed of 15 cockroaches). The results are given in Table 5.

TABLE 5

| Compound tested | | Insecticidal rate (%) | | |
|---|---|---|---|---|
| | | PB (0 μg) | PB (25 μg) | PB (50 μg) |
| Cpd. No. 8 of the present invention | (5 μg) | 0 | 14 | 25.6 |
| | (20 μg) | 0 | | |
| | (200 μg) | 97.7 | | |
| Allethrin | (5 μg) | 25.6 | | |
| | (20 μg) | 80 | | |

It is apparent that a potent synergistic effect can be obtained by the addition of piperonyl botoxide.

Example 16—House Fly

Increase in an Insecticidal Effect on Female Imagines of House Fly by the Additional of a Synergist of the Pyrethroid to Compound No. 6 of the Present Invention In a similar manner to that described in Example 10, the insecticidal rates of female imagines of house flies after 24 hours were determined by using compound No. 6 and piperonyl butoxide (PB) or cinepyrine-222 (S-222) (a synergist of the pyrethroid) in combination. The insects tested were 50 flies (two groups; each composed of 25 flies). The results are given in Table 6.

TABLE 6

| Cpd. Tested | Amount (μg) | Synergist (0 μg) | Insecticidal rate (%) | | | |
|---|---|---|---|---|---|---|
| | | | PB (2.5 μg) | PB (5 μg) | PB (10 μg) | S-222 (10 μg) |
| Invention Cpd. No. | | | | | 0 | 0 |
| 6 | 0.25 | 0 | 34 | | | |
| 6 | 0.5 | 0 | | 98 | | |
| 6 | 1 | 2 | | | 98 | 12 |
| 6 | 10 | 20 | | | | |
| Allethrin | 1 | 2 | | | | |
| Tetramethrin | 0.05 | 8 | | | | |
| | 0.1 | 28 | | | | |
| | 0.2 | 48 | | | | |

It is apparent that a potent synergistic activity can be exhibited when a synergist of the pyrethroid is added in an amount of 10 times that of a compound No. 6 to compound No. 6 of the present invention.

Example 17—House Mosquito Larva

Insecticidal Activity of Compound No. 6 of the Present Invention Against the Larva of Pale House Mosquitos 0.6 ml of an ethanol solution containing compound No. 6 of the present invention at a predetermined concentration was introduced into a deep petri dish of 9 cm in diameter and 6 cm in height, in which 30 larvae on the end stage of pale house mosquitos were swimming in 150 ml of water and the solution was well stirred. It was observed whether they were living or dead after 24, 48, 72 and 96 hours in a constant temperature chamber at 25° C. to determine the lethality rate. The results are given in Table 7.

TABLE 7

| Compound tested | Insecticidal rate (%) | | | |
|---|---|---|---|---|
| | 24 hr | 48 hr | 72 hr | 96 hr |
| compound No. 6 of present invention | | | | |
| (1 ppm) | 0.4 | 19.9 | 61.9 | 68.9 |
| (10 ppm) | 57.1 | 80.0 | 85.3 | 95.4 |
| (100 ppm) | 96.5 | 100 | 100 | 100 |

Example 18—House Fly

Insecticidal Test Against House Fly (*musca domestica Linné*) by an Ultralow Volume Dropping Method An acetone solution containing the composition of the present invention at a concentration given in Table 1 was applied to the background of the breast of each of female imagines of house fly (*Musca domestica Linné*), three- to five-day-old after emergence, anesthetized with carbon dioxide gas, by an Arnold's manual ultralow dropping device. The treated house flies were placed in a deep petri dish of 9 cm in diameter and 6 cm in height, on which bottom a filter paper was laid. Absorbent cotton containing 2% sugared water was placed in a container made of aluminum foil and given as a feed to the flies. The top of the dish was covered with gauze. 50 house flies (two groups; each being composed of 25) were left to stand in a room at about 23° C. After 24 and 48 hours, it was observed whether they were living or dead and the lethality rate was determined. The results are given in Table 8.

TABLE 8

| Pyrethroid tested | Lethality rate (%) | | | |
|---|---|---|---|---|
| | no compound of formula (8) | | compound of formula (8)* (1 μg) | |
| | after 24 hr | after 48 hr | after 24 hr | after 48 hr |
| tetramethrin (0.2 μg) | 52 | 50 | 54 | 54 |
| kadethrin (0.05 μg) | 78 | 54 | 94 | 80 |
| permethrin (0.01 μg) | 58 | 42 | 62 | 46 |
| allethrin (0.5 μg) | 46 | 48 | 76 | 74 |
| resmethrin (0.01 μg) | 66 | 82 | 72 | 74 |
| terarethrin (0.5 μg) | 2 | 2 | 18 | 30 |
| — | — | — | 0 | 0 |

*In all the examples, the endo-trimethylene isomer (6) was used.

EXAMPLE 19-House Fly

Insecticidal test against house fly (*Musca domestica Linné*) by an ultralow volume dropping method The procedure of Example 18 was repeated except that an acetone solution containing tetramethrin, the compound of formula (8) and piperonyl butoxide (PB) was applied to the house flies. After 24 hours, it was observed whether they were living or dead and the lethality rate was determined. The results are given in Table 9.

TABLE 9

| Composition tested | Lethality rate (%) after 24 hr |
| --- | --- |
| tetramethrin (0.05 μg) | 8 |
| compound (8) (0.25 μg) | 0 |
| PB (2.5 μg) | 0 |
| tetramethrin (0.05 μg) + compound (8) (0.25 μg) | 10 |
| compound (8) (0.25 μg) + PB (2.5 μg) | 34 |
| tetramethrin (0.05 μg) + PB (2.5 μg) | 78 |
| tetramethrin (0.05 μg) + compound (8) (0.25 μg) + PB (2.5 μg) | 92 |

EXAMPLE 20-House Fly

Insecticidal test against house fly (*Musca domestica* Linné) by an ultralow volume dropping method The procedure of Example 18 was repeated except that an acetone solution of the composition of the present invention consisting of tetramethrin and the compound of formula (8) at a concentration given in Table 3 was applied to the house flies. After 24 hours, it was observed whether they were living or dead and the lethality rate was determined. The results are given in Table 10.

TABLE 10

| Composition tested | Lethality rate (%) |
| --- | --- |
| tetramethrin (0.1 μg) | 6 |
| compound (8) (1 μg) | 2 |
| tetramethrin (0.1 μg) + compound (8) (1 μg) | 14 |
| allethrin (1 μg) | 8 |

EXAMPLE 21-German Cockroach

Insecticidal test against German cockroach (*Blattella germanica* Linné) by an ultralow volume dropping method An acetone solution containing the composition of the present invention consisting of tetramethrin and the compound of formula (8) at a concentration given in Table 11, was applied around the midlegs of the breast on the abdominal side of each of male imagines of German cockroaches (*Blattela germanica* Linné) anesthetized with carbon dioxide gas, by means of an Arnold's manual ultralow volume dropping device. The treated cockroaches were placed in an ice cream cup having 200 ml volume. Absorbent cotton containing 2% sugared water was given as a feed to them. The cup was covered with a lid through which fresh air could be freely passed. 20 cockroaches (two groups; each group being composed of 10 cockroaches) were left to stand in a room at about 23° C. After 74 hours, it was observed whether they were living or dead and the lethality rate was determined. The results are given in Table 11.

TABLE 11

| Composition tested | Lethality rate (%) |
| --- | --- |
| tetramethrin (0.1 μg) | 0 |
| tetramethrin (1 μg) | 10 |
| tetramethrin (0.1 μg) + compound (8) (6.25 μg) | 5 |
| tetramethrin (1 μg) + compound (8) (6.25 μg) | 15 |

In the following examples, parts are by weight unless otherwise stated.

EXAMPLE 22

1.0 part of Compound No. 6 of the present invention is blended with illuminating kerosene in such an amount as to make the resulting composition 100 parts to obtain an oil.

EXAMPLE 23

1.0 part of Compound No. 6 of the present invention and 5 parts of piperonyl butoxide is blended with illuminating kerosene in such an amount as to make the resulting composition 100 parts to obtain an oil.

EXAMPLE 24

20 parts of Compound No. 6 of the present invention, 10 parts of Sorpol® SM-200 (a product of Toho Kagaku K.K.) and 70 parts of xylene are mixed together with stirring to obtain a 20% emulsion. The emulsion is diluted 100-fold with water and then used.

EXAMPLE 25

1.0 part of Compound No. 6 os the present invention, 2.0 parts of IPM (isopropyl myristate) and 12 parts of talc are charged in an aerosol container. After a valve is fixed to the container, 85 parts of an aerosol propellant (liquefied petroleum gas) is introduced through the valve under pressure into the container to obtain an aerosol.

EXAMPLE 26

2 parts of Compound No. 8 of the present invention and 98 parts of clay are thoroughly crushed and mixed together to obtain a powder.

EXAMPLE 27

0.4 parts of tetramethrin and 1.0 part of the Compound of the formula (8) are blended with illuminating kerosene in such an amount as to make the resulting composition 100 parts to obtain an oil.

EXAMPLE 28

0.4 parts of tetramethrin, 1.0 part of the Compound of formula (8) and 5 parts of piperonyl butoxide are blended with illuminating kerosene in such an amount as to make the resulting composition 100 parts to obtain an oil.

EXAMPLE 29

5 parts of allethrin, 15 parts of the compound of formula (8), 10 parts of Sorpol® SM- ®(a product of Toho Kagaku K.K.) and 70 parts of xylene are mixed together with stirring to obtain a 20% emulsion.

EXAMPLE 30

0.4 parts of tetramethrin and 1.0 part of the Compound of formula (8) was dissolved in 28.6 parts of illuminating kerosene. The resulting solution is charged in an aerosol container. A valve is fixed to the container. Then 70 parts of an aerosol propellant (liquefied petroleum gas) is introduced into the container through the valve under pressure to obtain an aerosol.

EXAMPLE 31

0.4 parts of allethrin and 1.0 part of the compound of formula (8) was dissolved in 28.6 parts of illuminating kerosene. The resulting solution is charged in an aerosol container. After a valve is fixed to the container, 70 parts of an aerosol propellant (liquefied petroleum gas)

is introduced into the container through the valve under pressure to obtain an aerosol.

EXAMPLE 32

0.4 parts of tetramethrin, 1.0 part of the compound of formula (8) and 5.0 parts of piperonyl butoxide was dissolved in 23.6 parts of illuminating kerosene. The resulting solution is charged in an aerosol container. After a valve is fixed to the container, 70 parts of an aerosol propellent (liquefied petroleum gas) is introduced into the container through the valve under pressure to obtain an aerosol.

EXAMPLE 33

0.4 parts of allethrin, 1.0 part of the compound of formula (8) and 5.0 parts of piperonyl butoxide was dissolved in 23.6 parts of illuminating kerosene. The resulting solution is charged in an aerosol container. After a valve is fixed to the container, 70 parts of an aerosol propellant (liquefied petroleum gas) is introduced into the container through the valve under pressure to obtain an aerosol.

EXAMPLE 34

0.4 parts of allethrin, 1.0 of the compound of formula (8), 1.6 parts of sorbitan monolaurate and 15 parts of illuminating kerosene was mixed together with stirring. Further, 22 parts of distilled water is added thereto. The resulting solution is charged in an aerosol container. After a valve is fixed to the container, 60 parts of an aerosol propellant (liquefied petroleum gas) is introduced into the container through the valve to obtain an aerosol.

EXAMPLE 35

0.4 parts of allethrin, 1.0 part of the compound of the formula (8), 5.0 parts of piperonyl butoxide, 1.6 parts of soribtan monolaurate and 10 parts of illuminating kerosene was mixed together with stirring. Further, 22 parts of distilled water is added thereto. The resulting solution is charged in an aerosol container. After a valve is fixed to the container, 60 parts of an aerosol propellant (liquefied pertroleum gas) is introduced into the container through the valve under pressure to obtain an aerosol.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A tricyclic carboxylate ester of formula (I):

$$R_1\text{—COOR}_2 \quad (I)$$

wherein $R_1$ is a tricyclodecyl or tricycloundecyl group, and $R_2$ is a group of the formula

wherein $R_3$ is hydrogen or a cyano group;

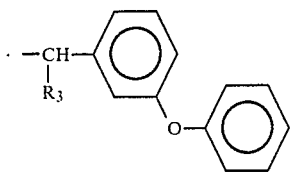

wherein $R_3$ is as defined above;

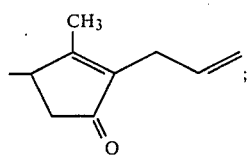

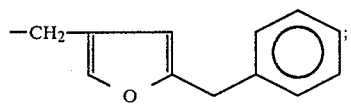

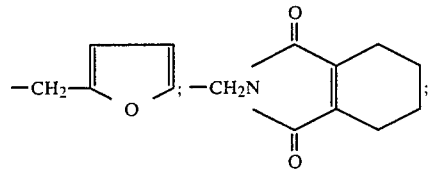

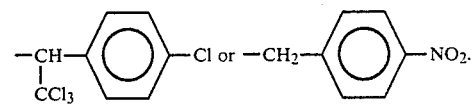

2. The tricyclic carboxylate ester as set forth in claim 1, wherein $R_1$ is a tricyclo[5.2.1.0$^{2,6}$]decyl or tricylco[3.3.3.1$^{3,7}$]decyl group.

3. The tricyclic carboxylate ester as set forth in claim 1, wherein $R_1$ is a tricyclo[4.3.1.1$^{2,5}$]undecyl or tricyclo[5.3.1.0$^{3,8}$]undecyl group.

4. The tricyclic carboxylate ester as set forth in claim 2, wherein said ester is α-cyano-3-phenoxybenzyl tricyclo[5.2.1.0$^{2,6}$]decane-2-carboxylate of the formula (8):

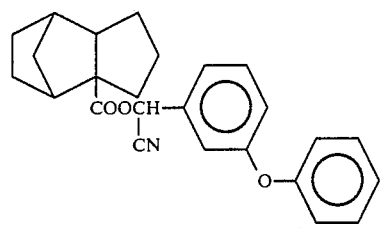

(8)

5. The tricyclic carboxylic ester as set forth in claim 4, wherein said ester is an endo-trimethylene isomer.

6. The tricyclic carboxylate ester as set forth in claim 4, wherein said ester is an exo-trimethylene isomer.

7. An insecticidal composition comprising: an effective insecticidal amount of a tricyclic carboxylate ester of formula (I):

$$R_1\text{—COOR}_2 \quad (I)$$

wherein $R_1$ is a tricyclodecyl or tricycloundecyl group, and $R_2$ is a group of the formula

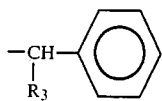

wherein R₃ is hydrogen or a cyano group;

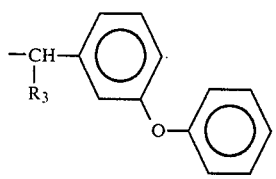

wherein R₃ is as defined above;

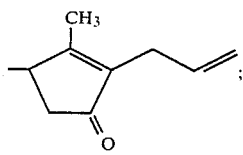

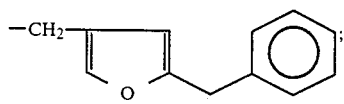

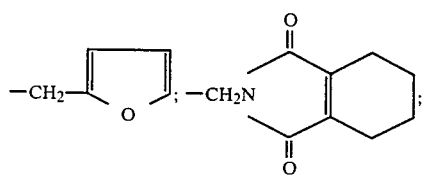

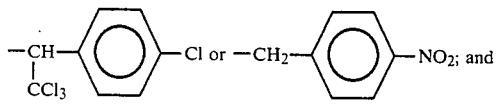

an acceptable carrier therefor.

8. The insecticidal composition as set forth in claim 7, and further including a fast-acting insecticide.

9. The insecticidal composition as set forth in claim 7, wherein the composition contains, as an active ingredient, α-cyano-3-phenoxybenzyl tricyclo[5.2.1.0²,⁶]decane-2-carboxylate of the formula (8):

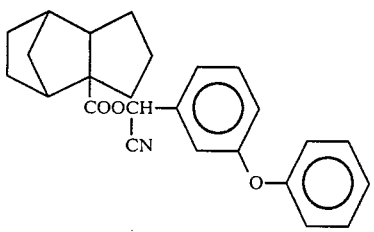

(8)

10. The insecticidal composition as set forth in claim 7, wherein the insecticidal composition contains a synergist or pyrethroid as an adjuvant.

11. The insecticidal composition as set forth in claim 9, wherein the insecticide composition contains a synergist or pyrethroid as an adjuvant.

12. An insecticidal composition, comprising: an effective insecticidal amount of a pyrethroid insecticide; and an effective insecticidal amount of α-cyano-3-phenoxybenzyl tricyclo[5.2.1.0²,⁶]decane-2-carboxylate of formula (8)

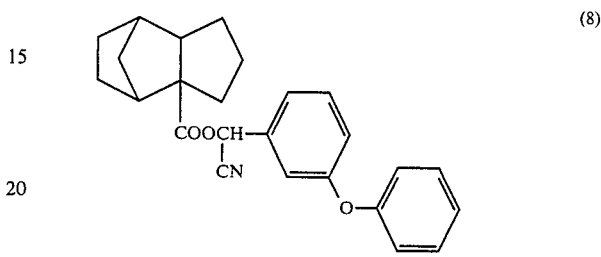

(8)

13. The insecticidal composition as set forth in claim 12, wherein the compound of formula (8) is an endo-trimethylene isomer.

14. The insecticidal composition as set forth in claim 12, wherein the compound of formula (8) is an exo-trimethylene isomer.

15. An insecticidal composition, comprising an effective insecticidal amount of a pyrethroid insecticide; an effective insecticidal amount of α-cyano-3-phenoxybenzyl tricyclo[5.2.1.0²,⁶]decane-2-carboxylate of formula (8)

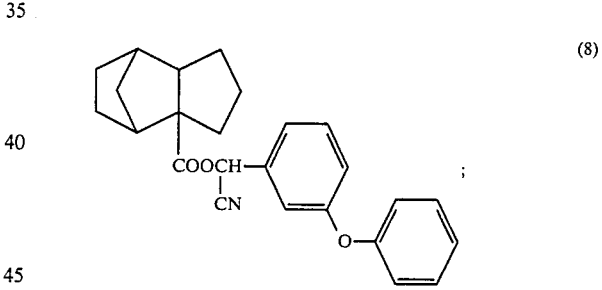

(8)

and piperonyl butoxide.

16. The insecticidal composition as set forth in claim 15, wherein the compound of formula (8) is an endo-trimethylene isomer.

17. The insecticidal composition as set forth in claim 15, wherein the compound of formula (8) is an exo-trimethylene isomer.

18. A method for killing insects which comprises applying an effective insecticidal amount of the compound of claim 1, to an area where insects are present.

19. A method for killing insects which comprises applying an effective insecticidal amount of the composition of claim 7, to an area where insects are present.

20. A method for killing insects which comprises applying an effective insecticidal amount of the composition of claim 8, to an area where insects are present.

* * * * *